United States Patent [19]

Snyder

[11] 3,953,591

[45] Apr. 27, 1976

[54] FATTY ACID, POLYSILOXANE AND WATER-SOLUBLE POLYMER CONTAINING SKIN CONDITIONING EMULSION

[75] Inventor: William Earl Snyder, Cincinnati, Ohio

[73] Assignee: The Procter & Gamble Company, Cincinnati, Ohio

[22] Filed: Apr. 29, 1974

[21] Appl. No.: 464,884

[52] U.S. Cl. ................................. 424/80; 424/73; 424/48; 424/81; 424/184; 424/362; 424/365
[51] Int. Cl.² .......................................... A61K 7/78
[58] Field of Search ................ 424/80, 81, 78, 184, 424/362, 365, 73

[56] References Cited
UNITED STATES PATENTS

| | | | |
|---|---|---|---|
| 3,320,133 | 5/1967 | Suga et al. | 424/365 |
| 3,335,053 | 8/1967 | Weitzel | 424/365 X |
| 3,535,427 | 10/1970 | Millar et al. | 424/365 |
| 3,660,566 | 5/1972 | Vinson et al. | 424/365 X |
| 3,697,644 | 10/1972 | Laiderman | 424/362 X |
| 3,835,169 | 9/1974 | Kraft et al. | 424/365 X |

*Primary Examiner*—Stanley J. Friedman
*Assistant Examiner*—Vera C. Clarke
*Attorney, Agent, or Firm*—Douglas C. Mohl; Ronald L. Hemingway; George W. Allen

[57] ABSTRACT

A synergistic skin conditioning emulsion composition comprising a fatty acid or a mixture of fatty acids, a polysiloxane fluid, a water-soluble polymer and water. The fatty acids, the polysiloxane and the water-soluble polymer combine to form a water-resistant barrier which allows skin to stay in a smooth and supple condition for an extended period of time.

9 Claims, No Drawings

FATTY ACID, POLYSILOXANE AND WATER-SOLUBLE POLYMER CONTAINING SKIN CONDITIONING EMULSION

FIELD OF THE INVENTION

The present invention relates to novel skin conditioning emulsion compositions which form a water-resistant barrier whereby the skin is kept in a smooth and supple condition for an extended period of time.

PRIOR ART

The treatment of human skin with various agents has been undertaken for many years with the goal being to keep the skin in a smooth and supple condition. Skin has the tendency to dry out when exposed to conditions of low humidity or to extended periods in a detergent solution. From a biochemical standpoint, dryness is a measure of the water content of the skin. Under normal conditions, the water content and vapor pressure of the epidermis are higher than those of the surrounding air with consequent evaporation of water from the skin surface. Skin becomes dry because of excessive loss of water from the surface and the subsequent loss of water from the stratum corneum.

Continuous and prolonged immersion in soap or detergent solutions may contribute to dryness of the stratum corneum. The reason for this is that the surfactant medium promotes dissolution of the skin surface lipids, the horny layer lipids, and the dissolution of the hygroscopic water-soluble components in the corneum.

To alleviate the aforementioned conditions, emollient creams as described in Sagarin, *Cosmetics, Science and Technology*, 2nd Edition, Vol. 1, Wiley Interscience (1972) have been recommended for application to the skin. The emollient materials probably increase the state of hydration of the corneous layer of the skin by altering the rate of diffusion of water from the lower epidermal and dermal layers, the rate of evaporation of water from the skin's surface, and the ability of the corneous layer to hold moisture.

Sagarin, at pages 27–104 and pages 179–222, discloses many emollient and hand lotion compositions containing some of the ingredients of the current invention, but not in the critical combination which is the basis of the current invention. Bennett, *The New Cosmetic Formulary*, Chemical Publishing Company, Inc., New York (1970), at page 74, discloses a formulation comprising fatty acids, a polysiloxane fluid, a neutralizing agent, lubricants, emollients, minors and water. Water-soluble polymers are disclosed for use in hand lotions in the aforementioned Sagarin reference, but it does not disclose the use of these polymers in the compositions of the present invention.

SUMMARY OF THE INVENTION

The present invention relates to a skin conditioning emulsion composition which utilizes a synergistic combination of ingredients to keep skin in a smooth and supple condition for an extended period of time. The conditioning composition of the present invention is an emulsion comprising a fatty acid or a mixture of fatty acids having an average carbon chain length of 10 to 31 carbon atoms wherein about 20% to about 80% of the acid groups are neutralized, a polysiloxane fluid having the formula — [$R_2SiO$] — wherein R is $C_1$–$C_4$ alkyl or phenyl and wherein said polysiloxane has a viscosity at 25°C. of from about 5 to about 2,000 centistokes, a water-soluble polymer having a molecular weight of from about 500 to about 5,000,000, and water, wherein the fatty acids and the polysiloxane fluid are present in a weight ratio of from about 12:1 to about 1:20 and comprise from about 0.35% to about 5.0% by weight of the total skin conditioning composition, while the water-soluble polymer comprises from about 0.015% to about 0.5%, and water comprises from about 50% to about 94.5% by weight of the total skin conditioning composition.

DETAILED DESCRIPTION OF THE INVENTION

The present invention can be broadly defined as a synergistic skin conditioning emulsion composition comprising:

A. a fatty acid or a mixture of fatty acids having an average carbon chain length of 10 to 31 carbon atoms wherein from about 20% to about 80% of the acid groups are neutralized;
B. a polysiloxane fluid having the formula — [$R_2SiO$] — wherein R is $C_1$–$C_4$ alkyl or phenyl and wherein said polysiloxane has a viscosity at 25°C. of from about 5 to about 2,000 centistokes;
C. a water-soluble polymer having a molecular weight of from about 500 to about 5,000,000; and
D. water, wherein (A) and (B) are present in a weight ratio of from about 12:1 to about 1:20 and comprise from about 0.35% to about 5.0% by weight of the total skin conditioning composition, while (C) comprises from about 0.015% to about 0.5% and (D) comprises, from about 50% to about 94.5% by weight of the total skin conditioning composition.

In a preferred embodiment, (A) and (B) are present in a ratio of about 1.5:1 and comprise from about 1% to about 3% by weight of the total skin conditioning composition, while (C) comprises from about 0.03% to about 0.10% and (D) comprises of about 65% to about 88% by weight of the total skin conditioning composition.

The fatty acids suitable for use in the compositions of the present invention contain an average of 10 to 31 carbon atoms in their chain. Examples of such acids are capric, undecyclic, lauric, myristic, palmitic and stearic. Preferred types of fatty acids are the lanolin fatty acids which include the following formulas:

$Ch_3 — (CH_2)_n — COOH$ ($n = 8$ to 24 inclusive);

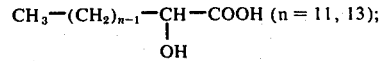

$CH_3—(CH_2)_{n-1}—\underset{\underset{OH}{|}}{CH}—COOH$ (n = 11, 13);

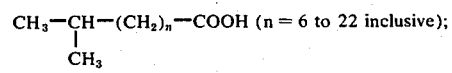

$CH_3—\underset{\underset{CH_3}{|}}{CH}—(CH_2)_n—COOH$ (n = 6 to 22 inclusive);

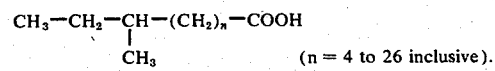

$CH_3—CH_2—\underset{\underset{CH_3}{|}}{CH}—(CH_2)_n—COOH$ (n = 4 to 26 inclusive).

As used herein, the term "lanolin fatty acids" means all of the fatty acids as shown above. These can be separated from lanolin by saponification as described in *Amerchol Lanolin Derivatives*, Vol. II (1971), Amerchol, a unit of CPC International, Inc., incorporated herein by reference. Amerchol markets lanolin fatty acids under the names Amerlate LFA and Amerlate WFA.

The acids may be neutralized either prior to their addition to the oil phase or in situ in the skin conditioning composition.

Any of a wide variety of water-soluble polymers can be used in the present invention. These include, for example, cellulose ethers, quaternary ammonium substituted cellulose ether derivatives as described in U.S. Pat. No. 3,472,840, Oct. 14, 1969, to Stone et al., incorporated herein by reference, hydroxyethyl cellulose, hydroxypropyl methyl cellulose, methyl cellulose, sodium carboxymethyl cellulose, acrylic polymers, polyvinyl pyrrolidone, polyvinyl alcohol, and polyvinylmethyl ether maleic anhydride. The polymers should have a molecular weight of about 500 to about 5,000,000.

Preferred water-soluble polymers are acrylic acid-/ethyl acrylate copolymers. Other preferred polymers are the carboxyvinyl polymers sold by the B. F. Goodrich Company under the trade mark of Carbopol resins. These resins consist essentially of a colloidally water-soluble polymer of acrylic acid crosslinked with from 0.75% to 2.00% of a crosslinking agent selected from the class consisting of polyallyl sucrose and polyallyl pentaerythritol. A most preferred polymer is Carbopol 934 which has an average molecular weight of about 3,000,000. Carbopol 934 is a water-soluble polymer of acrylic acid crosslinked with about 1% of a polyallyl ether of sucrose having an average of about 5.8 allyl groups for each sucrose molecule.

The polysiloxane fluids acceptable for use in the compositions of the present invention have the formula — $R_2SiO$] — wherein R is $C_1$–$C_4$ alkyl or phenyl and has a viscosity at 25°C. of from about 2,000 centistokes. A preferred polysiloxane is Silicone 200 Fluid (dimethyl polysiloxane) supplied by the Dow Corning Corporation, having a viscosity at 25°C. of about 350 centistokes.

The neutralizing agents suitable for use in neutralizing the fatty acids and acidic group containing water-soluble polymers of the present invention include those organic and inorganic bases which will form salts with the fatty acids and will neutralize the water-soluble polymer where such polymers contain free acid groups. Included in the group of such bases are sodium hydroxide, potassium hydroxide, ammonium hydroxide, monoethanol amine, diethanol amine and triethanol amine.

The skin conditioning emulsion compositions of the present invention may also contain emollient/humectant materials which serve to moisturize the skin, and materials which serve to make the compositions cosmetically acceptable. Included in the list of acceptable ingredients are emollient/humectant agents such as hydrocarbon oils and waxes, monoglyceride esters, triglyceride esters, acetoglyceride esters, ethoxylated glyceride, alkyl esters, alkenyl esters, fatty alcohols, fatty alcohol ethers, fatty acid esters of ethoxylated fatty alcohols, lanolin alcohols, sterols extracted from lanolin, lanolin esters, hydroxylated lanolin derivatives, polyhydric alcohols, polyether derivatives, polyhydric alcohol esters, wax esters, beeswax derivatives, vegetable waxes, phospholipids, sterols and amides. Preferred types of emollient/humectant materials are fatty alcohols containing from about 12 to about 18 carbon atoms such as lauryl, myristyl, cetyl and stearyl, and fatty acid esters of aliphatic alcohols where said esters contain from about 10 to about 31 carbon atoms such as ethyl laurate, isopropyl myristate, isopropyl palmitate, isopropyl behenate, isopropyl esters of lanolin fatty acids and hexadecyl acetate. These emollient-/humectant materials may comprise from about 0% to about 20% of the skin conditioning composition, preferably from about 1% to about 10%. The skin conditioning compositions may also contain such things as perfumes and preservatives such as propyl-p-hydroxybenzoate and methyl-p-hydroxy-benzoate at a level of about 0% to 1.0%, and coloring agents such as FD&C dyes and titanium dioxide at a level of about 0% to 0.5%.

The pH of the skin conditioning compositions may be from 4.5 to 8.0.

The water-soluble polymers, fatty acids, neutralizing agents and polysiloxane fluids are well known and are available commercially. The compositions of the present invention generally have a lotion consistency and may be in the form of oil-in-water or water-in-oil emulsions with the former being preferred because of their more pleasing cosmetic properties.

The compositions of the present invention are made by:

A. preparing the oil phase;
B. preparing the water phase; and
C. adding the oil phase to the water phase.

Step (A) is carried out by heating a proper mixture of fatty acids and polysiloxane to a temperature of about 75°C. to about 100°C. Step (B) is carried out by heating the water-soluble polymer in water to a temperature about the same as that of the oil phase. The emulsion is formed by slowly adding the oil phase prepared in step (A) to the water phase prepared in step (B) with stirring. Other ingredients may be added to the phase in which they are soluble prior to the mixing of the two phases or added directly to the mixed water and oil phases.

While not wishing to be limited to any particular theory, it is believed that the ingredients of the present invention form a longer-lasting protective barrier than do prior art compositions by utilizing the barrier properties of the individual ingredients in a synergistic manner. Thus, the benefits of the compositions are greater than one would expect from the individual components. The polymer forms a film in which the silicone fluid is likely interspersed while the fatty acids partly neutralized form a layer over the water-soluble polymer/silicone film and fill in the interstices of such film. This film matrix causes the skin to be less likely to become dry and scaly due to the film reducing evaporation of water from the surface of the skin and the corneous layers. The film is resistant to being washed off, thereby extending the duration of the skin conditioning benefits.

Specific examples embodying this invention follow and are not meant to be limiting. All percentages used herein in the specification and the claims are by weight unless otherwise specified.

EXAMPLE I

The following skin conditioning formulation was made and gave improved skin conditioning:

| Ingredient Part A | Percent by Weight |
| --- | --- |
| ¹Amerlate WFA (lanolin fatty acids) | 0.50 |
| ¹Amerlate W (isopropyl esters of lanolin fatty acids) | 0.75 |
| ¹Amerchol CAB (lanolin derived stearol extract and Petrolatum | 1.25 |

-continued

| Ingredient Part A | Percent by Weight |
|---|---|
| Stearic acid | 1.00 |
| Cetyl alcohol | 1.50 |
| Stearyl alcohol | 0.75 |
| [1]OH Lan (hydroxylated lanolin derivative, high OH value) | 0.25 |
| Isopropyl myristate | 1.25 |
| [2]Arlacel 165 (glycerol monostearate and polyoxyethylene stearate) | 0.75 |
| [3]Silicone 200 Fluid (dimethylpolysiloxane with viscosity at 25°C. of 350 centistokes) | 1.00 |

| Part B | Percent by Weight |
|---|---|
| [4]1.5% Carbopol 934 solution in H$_2$O (carboxy vinyl polymer with molecular weight of about 3,000,000) | 3.25 |
| Propylene glycol | 2.50 |
| 70% sorbitol solution in H$_2$O | 2.50 |
| Triethanolamine | 0.65 |
| Distilled water | 81.50 |

| Part C | Percent by Weight |
|---|---|
| Methyl paraben (methyl p-hydroxy benzoate - preservative) | 0.20 |
| Propyl paraben (Propyl p-hydroxy benzoate - preservative | 0.10 |
| Titanium dioxide | 0.20 |
| Perfume | 0.10 |

[1]All supplied by Amerchol, a unit of CPC International, Inc.
[2]Supplied by Atlas Chemicals, a division of ICI America, Inc.
[3]Supplied by Dow Corning Corporation
[4]Supplied by the B.F. Goodrich Company Parts A and B were heated separately to a temperature of 80°C. Part A was then added to Part B with stirring, forming an oil-in-water emulsion. Part C was then added to the mixture of Parts A and B. The result was a skin conditioning composition of increased effectiveness due to the synergistic activity of the silicone fluid, the fatty acids and the water-soluble polymer.

EXAMPLE II

The following formulation was prepared in the same manner as that described in Example I.

| Ingredient Part A | Percent by Weight |
|---|---|
| [1]Acetulan (acetylated lanolin) | 0.60 |
| [1]Amerlate P (isopropyl esters of lanolin fatty acids) | 0.20 |
| Stearic acid | 0.60 |
| [1]Amerlate WFA (lanolin fatty acids) | 0.15 |
| Cetyl alcohol | 2.00 |
| [2]Silicone 200 Fluid (dimethyl polysiloxane with viscosity at 25°C. of 350 centistokes) | 0.80 |

| Part B | Percent by Weight |
|---|---|
| [3]1.5% Carbopol 934 solution in H$_2$O (carboxy vinyl polymer with molecular weight of about 3,000,000) | 6.00 |
| Propylene glycol | 3.00 |
| Triethanolamine | 0.40 |
| Distilled water | 86.10 |

| Part C | Percent by Weight |
|---|---|
| Perfume | 0.10 |
| Titanium dioxide | 0.05 |

[1]All supplied by Amerchol, a unit of CPC International, Inc.
[2]Supplied by Dow Corning Corporation
[3]Supplied by B. F. Goodrich Company

EXAMPLE III

The following formulation was prepared in the same manner as that described in Example I.

| Ingredient Part A | Percent by Weight |
|---|---|
| [1]Amerlate WFA (lanolin fatty acids) | 0.50 |
| Stearic acid | 1.00 |
| [1]Amerlate W (isopropyl esters of lanolin fatty acids) | 0.75 |
| Cetyl alcohol | 1.50 |
| Stearyl alcohol | 0.75 |
| [1]OH Lan (hydroxylated lanolin derivative, high OH value) | 0.75 |
| Isopropyl myristate | 1.25 |
| [2]Arlacel 165 (glycerol monostearate and polyoxyethylene stearate) | 0.75 |
| [1]Amerchol CAB lanolin derived sterol extract and Petrolatum) | 1.25 |
| [3]Silicone 200 Fluid (dimethyl polysiloxane with viscosity at 25°C. of 350 centistokes) | 1.00 |

| Part B | Percent by Weight |
|---|---|
| [4]4% JR-1L resin | 3.50 |
| 70% sorbitol solution in H$_2$O | 2.50 |
| Propylene glycol | 2.50 |
| Triethanolamine | 0.65 |
| Distilled water | 80.85 |

| Part C | Percent by Weight |
|---|---|
| Propyl paraben (propyl p-hydroxybenzoate) | 0.20 |
| Methyl paraben (methyl p-hydroxybenzoate) | 0.10 |
| Titanium dioxide | 0.10 |
| Perfume | 0.10 |

[1]All supplied by Amerchol, a unit of CPC International, Inc.
[2]Supplied by Atlas Chemicals, a division of ICI America, Inc.
[3]Supplied by Dow Corning Corporation
[4]Supplied by the Union Carbide Corporation.

The description of the polymer is as follows:

JR-1L is a cationic cellulose ether derivative having a molecular weight in the range of 100,000 to 1,000,000 and the structure:

$$\left[ \begin{array}{ccc} R & R & R \\ | & | & | \\ O & O & O \\ \diagdown & | & \diagup \\ & R_{cell} & \end{array} \right]_y$$

wherein $R_{cell}$ is a residue of an anhydroglucose unit, wherein y is an integer of 50 to 20,000, and wherein each R individually represents a substituent of the formula:

$$-(C_2H_4O)_m-(CH_2CHO)_n-(C_2H_4O)_p-H$$
$$|$$
$$CH_2$$
$$|$$
$$CH_3N^{(+)}-CH_3Cl^{(-)}$$
$$|$$
$$CH_3$$

wherein m is an integer from 0 to 10, n is an integer of 0 to 3, and p is an integer of 0 to 10.

The composition given above can also be made using water-soluble polymers having a molecular weight of from 500 to 5,000,000 and selected from the group consisting of cellulose ethers, hydroxyethyl cellulose, hydroxypropyl cellulose, methyl cellulose, sodium carboxymethyl cellulose, polyvinyl pyrrolidone, polyvinyl alcohol, or polyvinyl methyl ether maleic anhydride, in place of JR-1L with an effective skin conditioning product being obtained.

What is claimed is:

1. A skin conditioning emulsion composition comprising:
   A. a fatty acid or a mixture of fatty acids having an average carbon chain length of 10 to 31 carbon atoms wherein from about 20% to about 80% of the acid groups are neutralized;
   B. a polysiloxane fluid having the formula — [$R_2SiO$] — wherein R is $C_1$–$C_4$ alkyl or phenyl and wherein said polysiloxane has a viscosity at 25°C. of from about 5 to about 2,000 centistokes;
   C. a water-soluble polymer having a molecular weight of about 500 to about 5,000,000 selected from the group consisting of quaternary ammonium substituted cellulose ether derivatives, hydroxyethyl cellulose, hydroxypropyl cellulose, a polymer of acrylic acid crosslinked with from 0.75% to 2.00% of a crosslinking agent selected from the group consisting of polyallyl sucrose and polyallyl pentaerythritol, methyl cellulose, sodium carboxymethyl cellulose, polyvinyl pyrrolidone, polyvinyl alcohol and polyvinyl methyl ether maleic anhydride; and
   D. water.

2. A skin conditioning emulsion composition as recited in claim 1 wherein the pH of the composition is from about 4.5 to about 8.

3. A skin conditioning emulsion composition as recited in claim 2 wherein the fatty acid or mixture of fatty acids is selected from the group consisting of capric, undecylic, lauric, myristic, palmitic, stearic and lanolin fatty acids.

4. A skin conditioning emulsion composition as recited in claim 2 wherein (A) and (B) are present in a weight ratio of about 1.5:1 and comprise from about 1.0% to about 3.0% by weight of the total skin conditioning composition, while (C) comprises from about 0.03% to about 0.10% and (D) comprises from about 65% to about 88% by weight of the total skin conditioning composition.

5. A skin conditioning emulsion composition comprising:

A. A fatty acid or mixtures of fatty acids selected from the group consisting of capric, undecylic, lauric, myristic, palmitic, stearic, and lanolin fatty acids, or mixtures of these acids, wherein 20% to about 80% of the acid groups are neutralized;
B. a polysiloxane fluid having the formula — [$R_2SiO$] — wherein R is $C_1$–$C_4$ alkyl or phenyl and wherein said polysiloxane has a viscosity at 25°C. of from about 5 to about 2,000 centistokes;
C. a water-soluble polymer of acrylic acid crosslinked with from 0.75% to 2.00% of a crosslinking agent selected from the group consisting of polyallyl sucrose and polyallyl pentaerythritol; and
D. water,
wherein (A) and (B) are present in a weight ratio of about 12:1 to about 1:20 and comprise from about 0.35% to about 5.0% by weight of the total skin conditioning composition, while (C) comprises from about 0.015% to about 0.5% and (D) comprises from about 50% to about 94.5% by weight of the total skin conditioning composition.

6. A skin conditioning emulsion composition as recited in claim 5 wherein (A) and (B) are present in a weight ratio of about 1.5:1 and comprise from about 1.0% to about 3.0% by weight of the total skin conditioning composition, while (C) comprises from about 0.03% to aout 0.10% and (D) comprises from about 65% to about 88% by weight of the total skin conditioning composition.

7. A skin conditioning emulsion composition as recited in claim 6 wherein an additional ingredient (E), an emollient/humectant material, is present in an amount from about 0% to about 20% by weight of the total skin conditioning composition.

8. A skin conditioning emulsion composition as recited in claim 7 wherein (E) is selected from the group consisting of fatty alcohols containing from about 12 to about 18 carbon atoms, fatty acid esters of aliphatic alcohols where said esters contain from about 10 to about 31 carbon atoms, and mixtures of these ingredients, and is present in an amount of from about 1% to about 10%.

9. A skin conditioning emulsion composition as recited in claim 6 wherein (C) is an acrylic acid polymer crosslinked with about 1% of a polyallyl ether of sucrose having an average of about 5.8 allyl groups for each sucrose molecule.

* * * * *